(12) United States Patent
Gatten

(10) Patent No.: US 7,614,788 B2
(45) Date of Patent: *Nov. 10, 2009

(54) APPARATUS AND METHOD FOR PROVIDING A SHIELDING MEANS FOR AN X-RAY DETECTION SYSTEM

(75) Inventor: Ronald A. Gatten, Pleasanton, CA (US)

(73) Assignee: GE Security, Inc., Bradenton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/136,601

(22) Filed: Jun. 10, 2008

(65) Prior Publication Data

US 2008/0310586 A1    Dec. 18, 2008

Related U.S. Application Data

(63) Continuation of application No. 11/298,925, filed on Dec. 9, 2005, now Pat. No. 7,384,194.

(51) Int. Cl.
*H05G 1/00* (2006.01)
*H01J 35/16* (2006.01)

(52) U.S. Cl. .......................... 378/208; 378/57; 378/203

(58) Field of Classification Search .................. 378/4, 378/20, 51, 53–55, 57, 95, 114, 117, 203, 378/208, 210
See application file for complete search history.

(56) References Cited

U.S. PATENT DOCUMENTS 3,832,545 A * 8/1974 Bartko ........................ 376/159

(Continued)

FOREIGN PATENT DOCUMENTS

| EP | 1151919 A1 | 11/2001 |
|---|---|---|
| WO | 9933723 | 7/1999 |
| WO | 2006015381 A2 | 2/2006 |
| WO | 2007090450 A1 | 8/2007 |

OTHER PUBLICATIONS

International Search Report, PCT US2007/069846, dated Jan. 29, 2009, 4 pages.

*Primary Examiner*—Edward J Glick
*Assistant Examiner*—Thomas R Artman
(74) *Attorney, Agent, or Firm*—Armstrong Teasdale LLP

(57) ABSTRACT

An apparatus and method for providing an x-ray shield means in an x-ray detection system. An x-ray inhibiting container for use in a computed tomography system is provided, the container comprising: a peripheral wall; and a bottom, wherein the peripheral wall and bottom define a receiving area, and a forward portion and a rearward portion of the peripheral wall comprise an x-ray inhibiting material. The system comprising: a computed tomography scanner, configured to produce x-ray projection data as an object is passed through the computed tomography scanner, the computed tomography scanner comprising: a gantry having an opening; and an x-ray source configured to project a fan beam of x-rays towards a detector array disposed on an opposite side of the gantry opening, the x-ray source and detector array being mounted to the gantry about the opening; a structure defining an internal volume being configured to receive at least the gantry of the computed tomography scanner therein, the structure having an input opening and an outlet opening, the structure comprising an x-ray shielding material; and a motorized conveyor for passing a plurality of tubs through the input opening to the outlet opening, wherein each of the tubs comprises a peripheral wall and a bottom to define a tub volume and a forward portion and a rearward portion of the peripheral wall is configured to substantially cover the input opening or the outlet opening as the plurality of tubs are passed through the structure, wherein the forward portion and the rearward portion each comprise an x-ray shielding material.

13 Claims, 5 Drawing Sheets

U.S. PATENT DOCUMENTS

| | | |
|---|---|---|
| 5,182,764 A | 1/1993 | Peschmann et al. |
| 5,367,552 A | 11/1994 | Peschmann |
| 5,796,802 A | 8/1998 | Gordon |
| 5,960,056 A | 9/1999 | Lai |
| 6,647,084 B1 | 11/2003 | Hsieh |
| 6,647,091 B2 | 11/2003 | Fenkart et al. |
| 6,859,518 B2 * | 2/2005 | Banchieri et al. ............. 378/57 |
| 6,872,001 B1 | 3/2005 | Gilevich |
| 6,922,461 B2 * | 7/2005 | Kang et al. .................... 378/57 |
| 7,062,011 B1 * | 6/2006 | Tybinkowski et al. ......... 378/57 |
| 7,313,221 B2 | 12/2007 | Sowerby et al. |
| 7,384,194 B2 * | 6/2008 | Gatten ........................ 378/208 |
| 7,415,094 B2 | 8/2008 | Johnson et al. |
| 7,418,077 B2 | 8/2008 | Gray |
| 2008/0267350 A1 * | 10/2008 | Gray ........................... 378/57 |

* cited by examiner

APPARATUS AND METHOD FOR PROVIDING A SHIELDING MEANS FOR AN X-RAY DETECTION SYSTEM

CROSS-REFERENCE TO RELATED APPLICATIONS

This application is a continuation of U.S. patent application Ser. No. 11/298,925, filed Dec. 9, 2005, now U.S. Pat. No. 7,384,194, which is hereby incorporated by reference.

BACKGROUND

This present invention relates generally to an apparatus and method for scanning and inspecting baggage. More particularly, the present invention relates to security screening systems for use at airports.

Carry-on baggage inspection systems generally utilize a scan projection (SP) image for presentation to the operator. In most baggage inspection systems, scan projection images are created by moving an object under a fan beam of x-rays from a stationary x-ray source.

In some computed tomography (CT) imaging system configurations, an x-ray source projects a fan-shaped beam which is collimated to lie within an X-Y plane of a Cartesian coordinate system and generally referred to as an "imaging plane". The x-ray beam passes through an object being imaged. The beam, after being attenuated by the object, impinges upon an array of radiation detectors. The intensity of the attenuated radiation beam received at the detector array is dependent upon the attenuation of the x-ray beam by the object. Each detector element of the array produces a separate electrical signal that is a measurement of the beam intensity at each detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements (e.g., projection data), from the detector array at one gantry angle is referred to as a "view". A "scan" of the object comprises a set of views made at different gantry angles, or view angles, during one revolution of the x-ray source and detector about the object or patient being imaged.

To perform a "helical" scan, the object is continually moved via a conveyor belt while the projection data for the prescribed number of slices is acquired. The helix mapped out by the fan beam yields projection data from which images in each prescribed slice may be reconstructed. Orthographic and scan projection SP-like images can be created from helical scan data by reconstruction of the entire volume, and projecting digitally through the reconstructed volume.

During the scanning of the object, potentially harmful X-ray beams are shielded by the structure of apparatus surrounding the conveyor belt and shielding means disposed at the apparatus entry and exit points (e.g., curtains disposed on the entry and exit points). In order to provide the necessary shielding an x-ray blocking material (e.g., lead, aluminum, carbon fibers or any other material that inhibits X-rays) is disposed in the apparatus structure and the curtains disposed at the entry and exit points.

However, these curtains may obstruct the flow of baggage on the conveyor as they may cause lighter objects (e.g., smaller bags, purses, carry on luggage, etc.) to tumble or even stop on the conveyor. This is exacerbated if such a device were to be used as an initial security screening measure at airport check in as typically smaller objects, purses, coats, shoes, laptops must be placed on the conveyor for x-ray screening.

Accordingly, it is desirable to provide an apparatus and method for providing an x-ray shielding means that does not interfere with the throughput of objects through the scanning system.

SUMMARY OF THE INVENTION

An apparatus and method for providing an x-ray shield means in an x-ray detection system. An x-ray inhibiting container for use in a computed tomography system is provided, the container comprising: a peripheral wall; and a bottom, wherein the peripheral wall and bottom define a receiving area, and a forward portion and a rearward portion of the peripheral wall comprise an x-ray inhibiting material.

The system comprising: a computed tomography scanner, configured to produce x-ray projection data as an object is passed through the computed tomography scanner, the computed tomography scanner comprising: a gantry having an opening; and an x-ray source configured to project a fan beam of x-rays towards a detector array disposed on an opposite side of the gantry opening, the x-ray source and detector array being mounted to the gantry about the opening; a structure defining an internal volume being configured to receive at least the gantry of the computed tomography scanner therein, the structure having an input opening and an outlet opening, the structure comprising an x-ray shielding material; and a motorized conveyor for passing a plurality of tubs through the input opening to the outlet opening, wherein each of the tubs comprises a peripheral wall and a bottom to define a tub volume and a forward portion and a rearward portion of the peripheral wall is configured to substantially cover the input opening or the outlet opening as the plurality of tubs are passed through the structure, wherein the forward portion and the rearward portion each comprise an x-ray shielding material.

A computed tomography system for scanning items, the system comprising: a computed tomography scanner, configured to produce x-ray projection data as an object is passed through the computed tomography scanner, the computed tomography scanner comprising: a gantry having an opening; and an x-ray source configured to project a fan beam of x-rays towards a detector array disposed on an opposite side of the gantry opening, the x-ray source and detector array being rotatably mounted about the opening; a structure defining an internal volume being configured to receive at least the gantry of the computed tomography scanner therein, the structure having an input opening and an outlet opening, the structure comprising an x-ray shielding material; and a motorized conveyor for passing a plurality of tubs through the input opening to the outlet opening, wherein each of the tubs comprises a peripheral wall and a bottom to define a tub volume and a forward portion and a rearward portion of the peripheral wall is configured to substantially cover the input opening and the outlet opening as the plurality of tubs are passed through the structure, wherein the forward portion and the rearward portion each comprise an x-ray shielding material and each of the plurality of tubs further comprises a pair of side walls each extending between the forward portion and the rearward portion; an indicator disposed on each of the plurality of tubs at a discrete location; and a plurality of scanners each being configured and located to detect the presence of the indicator of one of the plurality of tubs at a discrete location within the structure, wherein a first one of the plurality of scanners provides a first signal when a first one of the plurality of tubs is located proximate to the input opening and the x-ray shielding material of the first tub is disposed within the input opening and a second one of the plurality of scanners provides a second signal when a second one of the plurality of tubs is located proximate to the opening of the gantry and a third one of the plurality of scanners provides a third signal when a third one of the plurality of tubs is disposed proximate to the outlet opening and the x-ray shield material of the tub is disposed within the outlet, and wherein the x-ray source is prevented from projecting the fan beam of x-ray unless the first, the second and the third signals are generated.

A computed tomography system for scanning items, the system comprising: a computed tomography scanner, configured to produce x-ray projection data as an object is passed through the computed tomography scanner, the computed tomography scanner comprising: a gantry having an opening; and an x-ray source configured to project a fan beam of x-rays towards a detector array disposed on an opposite side of the gantry opening, the x-ray source and detector array being mounted to the gantry about the opening; a structure defining an internal volume being configured to receive at least the gantry of the computed tomography scanner therein, the structure having an input opening and an outlet opening, the structure comprising an x-ray shielding material; and a motorized conveyor for passing a plurality of tubs through the input opening to the outlet opening, wherein each of the tubs comprises a peripheral wall and a bottom to define a tub volume and a forward portion and a rearward portion of the peripheral wall is configured to substantially cover the input opening or the outlet opening as the plurality of tubs are passed through the structure, wherein the forward portion and the rearward portion each comprise an x-ray shielding material.

A method for shielding x-rays of a computed tomography system, the method comprising: advancing a plurality of a plurality of tubs through an input opening and an outlet opening of the computed tomography system, wherein each of the plurality of tubs are substantially uniform in at least one dimension and each of the plurality of tubs comprises a peripheral wall and a bottom to define a tub volume and a forward portion and a rearward portion of the peripheral wall is configured to substantially cover the input opening and the outlet opening of the computed tomography system, wherein the forward portion and the rearward portion each comprise an x-ray shielding material and each of the plurality of tubs further comprises a pair of side walls each extending between the forward portion and the rearward portion and an indicator disposed on the at least one dimension of each of the plurality of tubs; determining the location of each of the plurality of tubs passing through the computed tomography system by scanning for the indicator; and generating an output signal when either the input opening and the outlet opening is covered by either a forward portion or the rearward portion of one of the plurality of tubs, wherein an x-ray source of the computed tomography system is prevented from generating an x-ray beam unless the output signal is generated.

DETAILED DESCRIPTION OF EXEMPLARY EMBODIMENTS

The disclosure of the present invention relates to an apparatus and method for providing a shielding means for use with x-ray detection systems. In particular, the shielding means is contemplated for use with security checkpoint systems configured to scan luggage, carry on luggage and other items being loaded onto an airplane.

Accordingly, exemplary embodiments of the present invention are directed to bins or tubs configured to hold the items being scanned while the bin or tub comprises a portion of the x-ray shielding of the scanning device. In addition, exemplary embodiments of the present invention are also contemplated to provide a method for determining when an object or tub is in the proper location for scanning and the appropriate shielding is in place. Moreover, additional exemplary embodiments provide methods for increasing the throughput of the scanning device.

Figure 1:
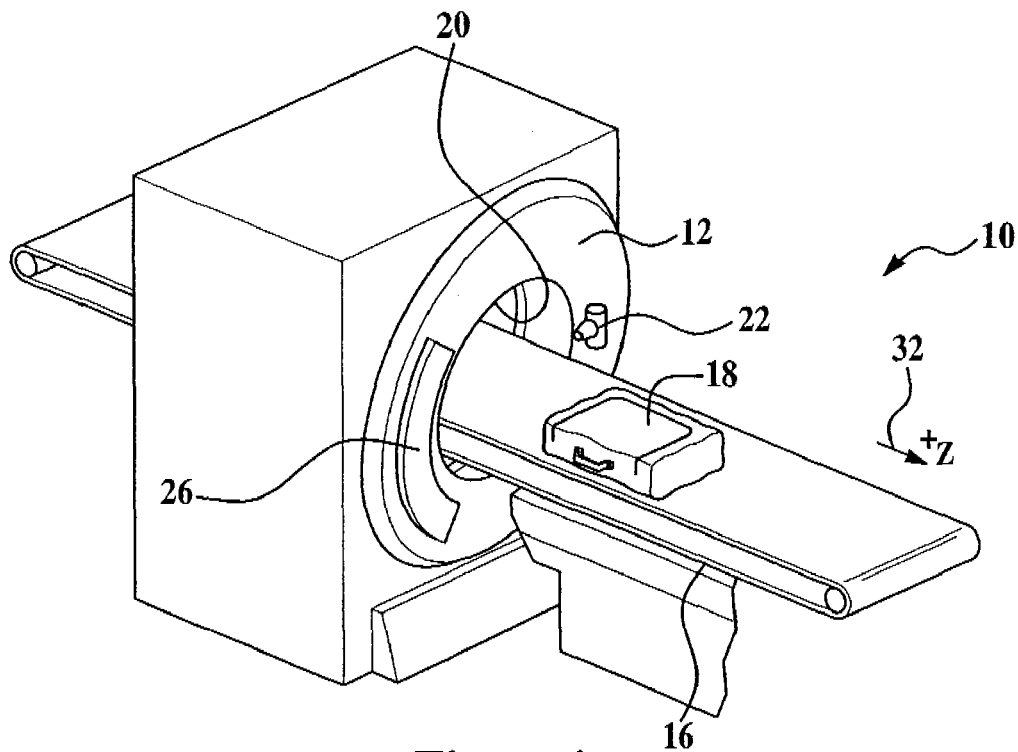
FIGS. 1 and 2 are schematic illustrations of a CT scanning system.
Figure 2:
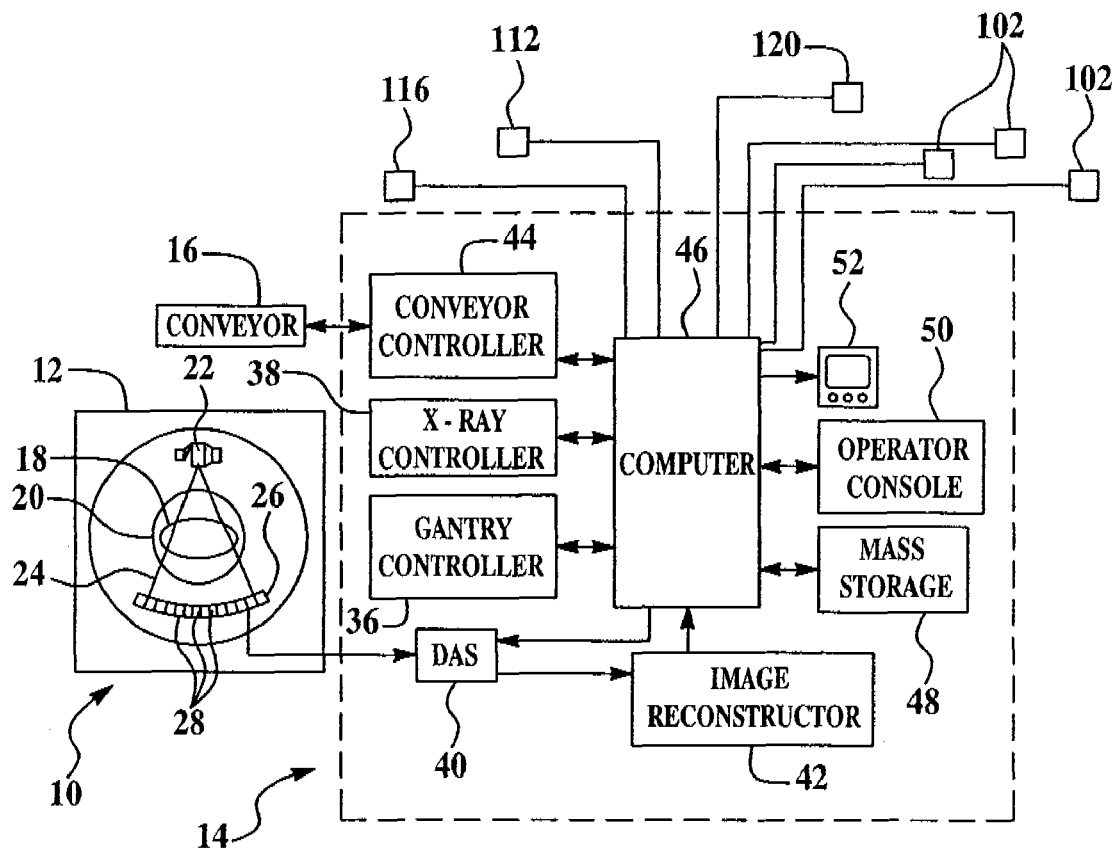

Referring now to FIGS. 1 and 2, a computed tomography (CT) imaging system 10 is shown. FIGS. 1 and 2 are intended to provide a non-limiting example of a CT imaging system. CT imaging system 10 is shown having a gantry 12, which is representative of a CT scanner, a control system 14, and a motorized conveyor 16 for positioning an object 18, such as a piece of luggage, in gantry opening 20 in gantry 12. Gantry 12 includes an x-ray source 22 that projects a fan beam of x-rays 24 toward a detector array 26 on the opposite side of gantry 12. Detector array 26 is formed by detector elements 28. Detector elements 28 are radiation detectors that each produces a signal having a magnitude that represents and is dependent on the intensity of the attenuated x-ray beam after it has passed through object 18 being imaged. During a helical scan that acquires x-ray projection data, the gantry along with the x-ray source and detector array rotate within the imaging plane and around the object about a center of rotation 30, while the object is moved through the gantry in a z-direction 32 perpendicular to the imaging plane.

Gantry 12 and x-ray source 22 are controlled by control system 14, which includes a gantry controller 36, an x-ray controller 38, a data acquisition system (DAS) 40, an image reconstructor 42, a conveyor controller 44, a computer 46, a mass storage-system 48, an operator interface 50, and a display device 52. The gantry controller controls the rotational speed and position of the gantry, while the x-ray controller provides power and timing signals to the x-ray source, and the data acquisition system acquires analog data from the detector elements and converts the data to digital form for subsequent processing. The image reconstructor receives the digitized x-ray data from the data acquisition system and performs an image reconstruction process that involves filtering the projection data by using a helical reconstruction algorithm.

Computer 46 is in operable communication with the gantry controller, the x-ray controller, and the conveyor controller whereby control signals are sent from the computer to the controllers and information is received from the controllers by the computer. The computer also provides commands and operational parameters to the data acquisition system and receives a reconstructed image data from the image reconstructor. The reconstructed image data is stored by the computer in the mass storage system for subsequent retrieval. An operator interfaces with the computer through the operator interface, which may include, for example, a keyboard and a graphical pointing device, and receives output, such as, for example, a reconstructed image, control settings and other information, on the display device.

Operable communication between the various system elements of FIG. 2 is depicted by arrowhead lines, which illustrate a means for either signal communication or mechanical operation, depending on the system element involved. Operable communication amongst and between the various system elements may be obtained through a hardwired or a wireless arrangement. The computer may be a standalone computer or a network computer and may include instructions in a variety of computer languages for use on a variety of computer platforms, such as, for example, DOS-based systems, Apple-based systems, Windows-based systems, UNIX-based systems, or the like. Other examples of the computer include a system having a microprocessor, microcontroller or other equivalent processing device capable of executing commands of computer readable data or program for executing a control algorithm. In order to perform the prescribed functions and desired processing, as well as the computations therefore (e.g., the execution of fourier analysis algorithm(s), the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include input signal filtering to enable accurate sampling and conversion or acquisitions of such signals from communications interfaces. As described above, exemplary embodiments of the present invention can be implemented through computer-implemented processes and apparatuses for practicing those processes.

Figure 3:
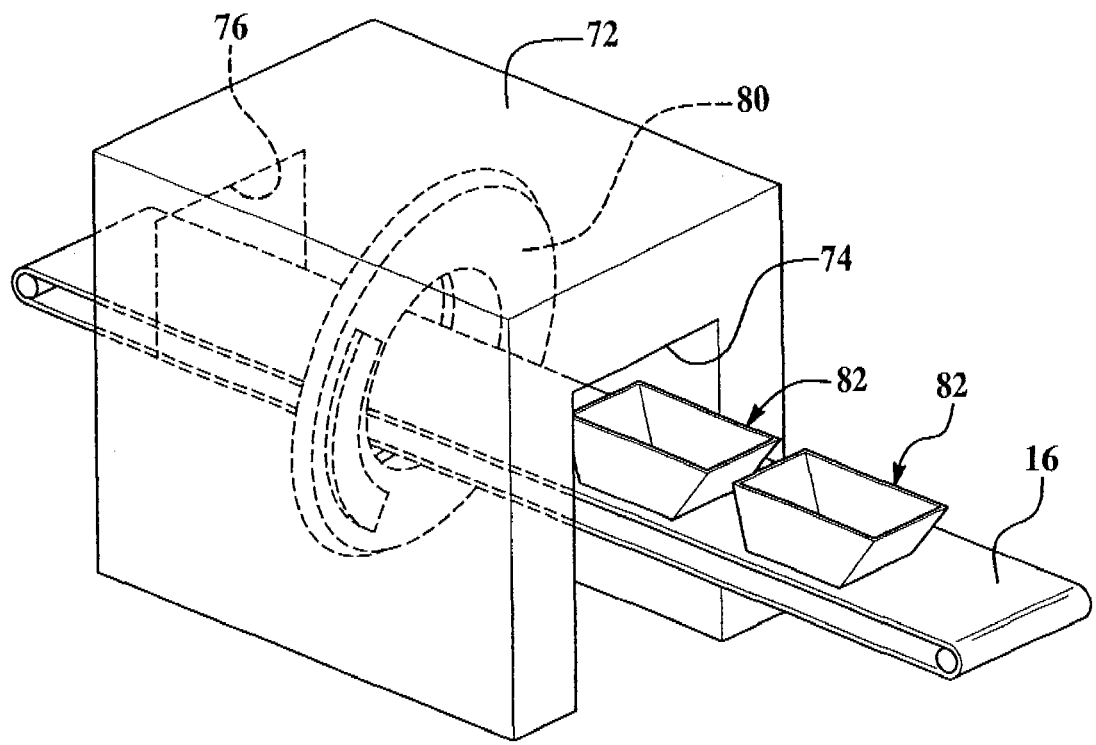
FIG. 3 is a perspective view of a CT scanning system in accordance with an exemplary embodiment of the present invention.
Figure 4:
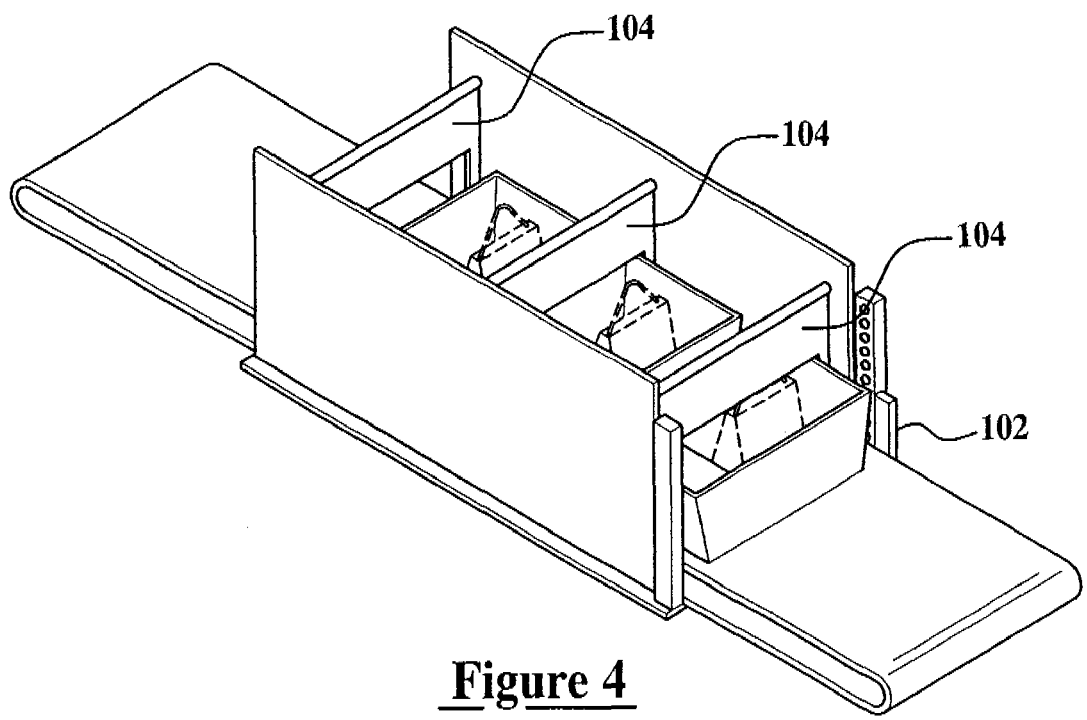
FIGS. 4 and 5 are partial perspective views of an exemplary embodiment of the present invention.
Figure 5:
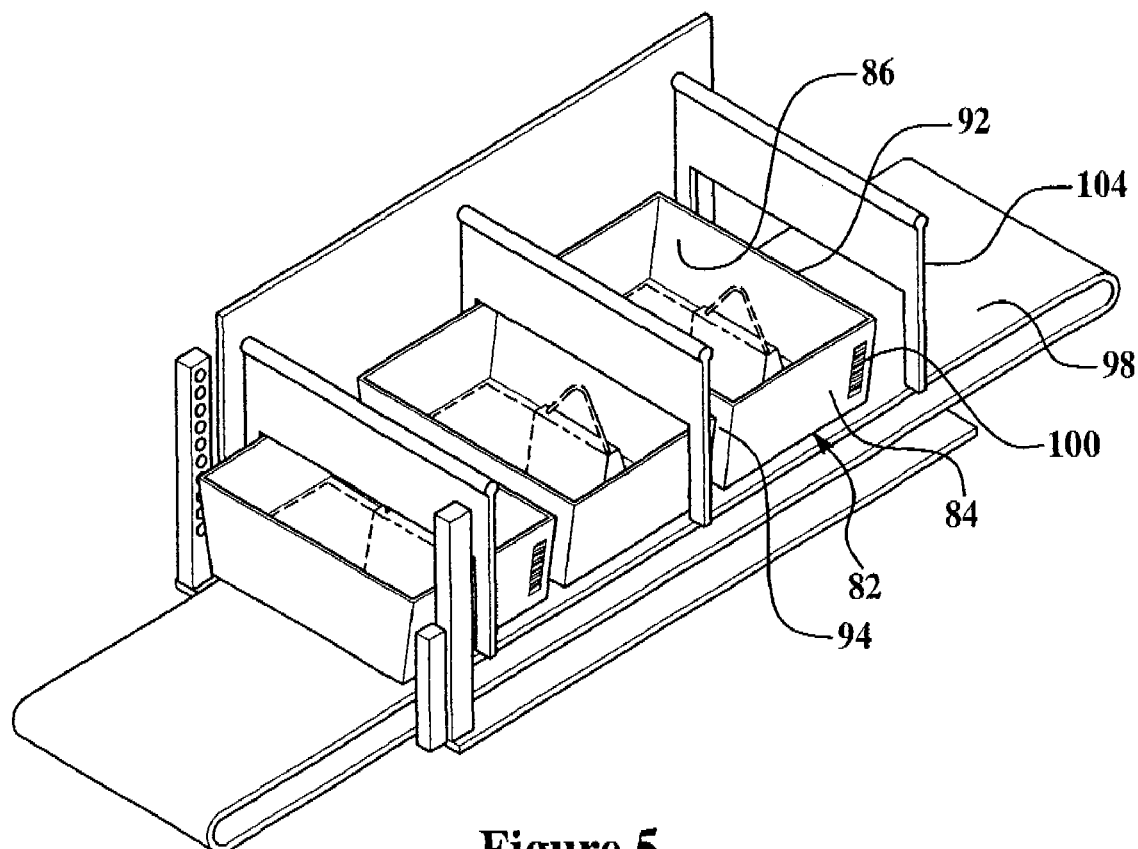
Figure 6:
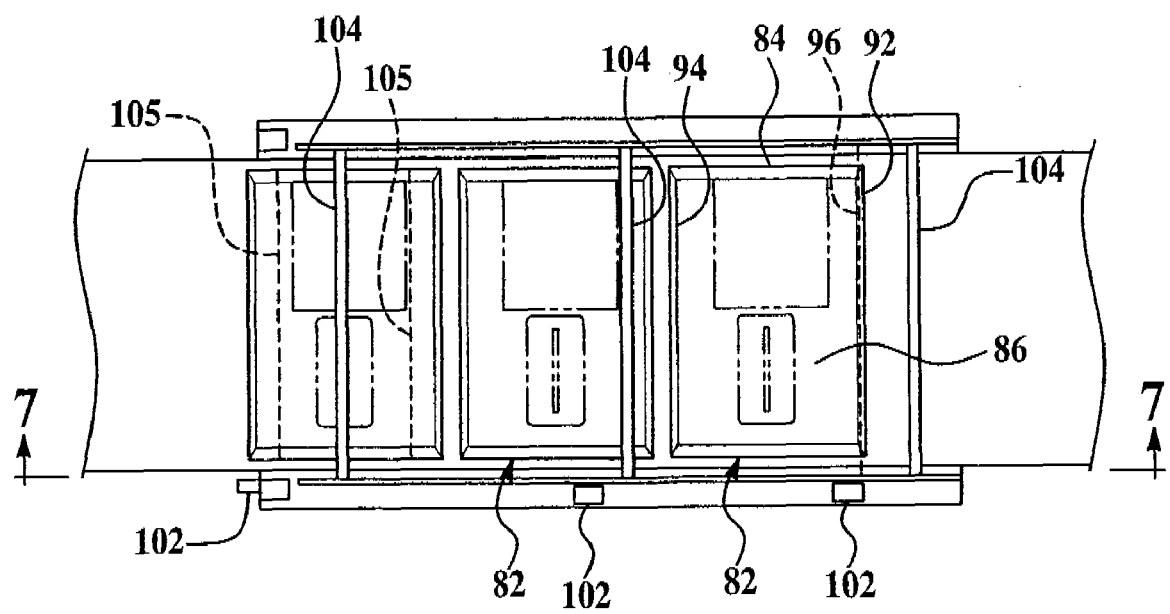
FIG. 6 is a top plan view of an exemplary embodiment of the present invention.
Figure 7:
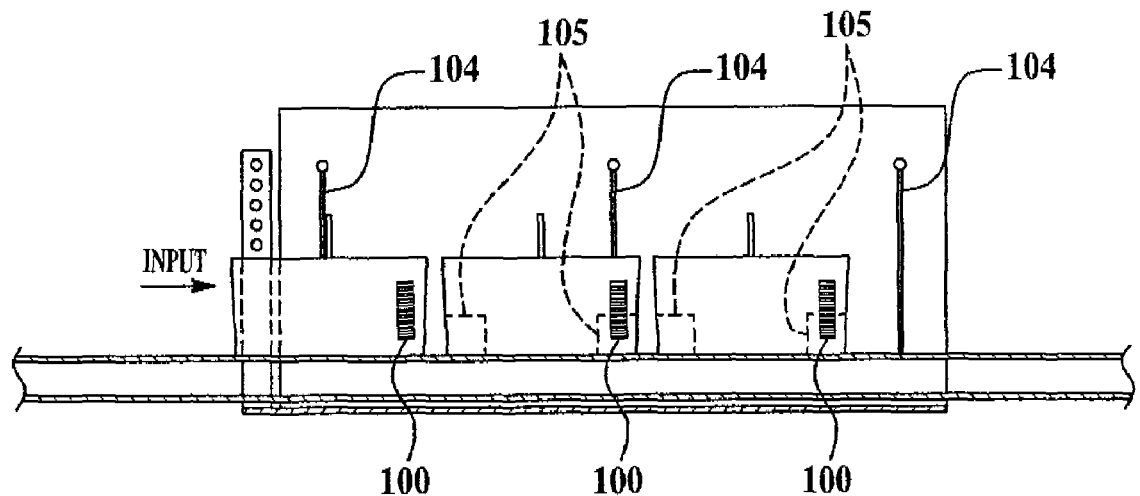
FIG. 7 is a view along lines 7-7 of FIG. 6.

Referring now to FIG. 3, a perspective view of CT scanning system and an x-ray inhibiting container constructed in accordance with an exemplary embodiment of the present invention is illustrated. As illustrated, a CT scanning system 70 has a structure 72 configured to receive therein at least a gantry of a CT scanner, wherein the gantry comprises an x-ray source that projects a fan beam of x-rays toward a detector array on the opposite side of the gantry. As previously discussed, a non-limiting example of one such gantry and CT scanner is illustrated in FIGS. 1 and 2.

As previously discussed, it is desirable to protect the CT scanner operator and individuals from x-rays generated by the x-ray source. Thus, and in accordance with an exemplary embodiment, structure 72 will comprise x-ray inhibiting materials in order to provide the desired x-ray shielding while allowing for x-ray scanning of objects. However, and in order to pass objects through the system, the structure is configured to have an input opening 74 and an outlet opening 76, which are configured to allow objects placed on a motorized conveyor belt 78 to pass into opening 74, through a gantry opening 80 for CT scanning and thereafter out outlet opening 76.

One non-limiting contemplated use for system 70 is a luggage or object screening means for screening carry on objects of passengers embarking on airline flights, wherein the carry on luggage or other items are screened/checked for prohibited items. Accordingly, a passenger would place their objects on the conveyor for scanning by the CT system wherein the objects travel into the input opening and out the outlet opening when the scanning is complete.

Referring now to FIGS. 3-7, and in order to provide a means for effectively blocking the input and outlet openings of the structure of the CT scanning system, a plurality of containers or tubs 82 are provided. FIGS. 4-7 provide non-limiting illustrations of portions of structure 72 with sections removed for clarity. For example, the structure illustrated in FIGS. 4-7 provides a non-limiting configuration of a portion of structure 72 or may comprise a separate structure within the structure 72 of FIG. 3. In other words, the end openings illustrated in FIGS. 4-7 may comprise openings 74 and 76 or alternatively may be additional openings within structure 72 of FIG. 3.

Nevertheless and in accordance with exemplary embodiments of the present invention and in order to protect the CT scanner operator and individuals from x-rays generated by the x-ray source structure 72 will comprise x-ray inhibiting materials in order to provide the desired x-ray shielding while allowing for x-ray scanning of objects and each tub or container will be configured to locate an x-ray inhibiting material proximate to the input and output openings of the structure housing the CT scanner or a structure within the structure housing the CT scanner. It is also understood that exemplary embodiments of the present invention may be used with other types of x-ray scanning devices and that the present invention is not limited to CT scanners.

In accordance with an exemplary embodiment each tub or container will comprise a peripheral wall 84 and a bottom 86, wherein the peripheral wall and the bottom define a receiving area 88. The receiving area 88 being configured to receive a plurality of articles 90 therein for CT scanning, non-limiting examples of such articles include lap tops, purses, carry on luggage etc. In addition, each tub or container will comprise a forward portion 92 and a rearward portion 94, each of which comprises a portion of the peripheral wall. In accordance with an exemplary embodiment, forward portion 92 and a rearward portion 94 will also comprise an x-ray inhibiting material 96 located within or comprising forward portion 92 and rearward portion 94. In accordance with an exemplary embodiment the x-ray inhibiting material is lead and in one exemplary embodiment, the x-ray inhibiting material is integrally molded therein during for example an injection molding of the tub 82. One non-limiting example of a material contemplated for tub 82 is an easily molded material such as plastic, which will also be lightweight and durable.

In accordance with an exemplary embodiment, the forward portion and the rearward portion of each tub is configured to substantially block the input opening or outlet opening of the structure when positioned proximate thereto. Thus, tubs 82 will provide a means for effectively blocking the input and outlet openings and since the forward and rearward portions of the tubs are configured to have an x-ray inhibiting material the tubs will block leakage of spurious x-rays from the CT scanner. In addition, and since tubs 96 will block the openings when disposed proximate thereto, there no longer is a need to use passive x-ray shielding curtains, which as discussed herein may be dragged inwardly by the item being scanned or the curtains themselves may cause smaller objects to become toppled over or dragged on the conveyor belt. Moreover, such toppled bags or objects may ultimately cause a jam within the scanning system, wherein the scanner must be shut down and while the objects are cleared from their jammed position.

Although the tubs are shown as being rectangular, it is contemplated that any configuration of tub is considered to be within exemplary embodiments of the present invention, as long as each tub comprises a forward and rearward portion configured to substantially block the input and outlet openings while providing a means for blocking x-rays as the tubs are passed through the CT scanner on a motorized conveyor 98.

In addition, and in accordance with another exemplary embodiment of the present invention and in order to determine the location of the plurality of tubs as they are passed through the system, an indicator 100 is disposed on a surface of the tub. In accordance with an exemplary embodiment indicator 100, will comprise machine readable code that is detectable by a scanning device 102, located on structure 72 in order to scan for and detect indicator 100.

In accordance with an exemplary embodiment the indicator and scanner will be located to detect a particular location of tub 82 on conveyor 98 (e.g., a position wherein either the forward or rearward portion of the tub is located to effectively disposed the x-ray inhibiting material of the tub at the inlet or outlet of the structure). One exemplary way of achieving this is to dispose the indicator in substantially the same location on each of the tubs and locate the scanner or its field of view such that once the presence of the indicator is detected it is known that the tub will have its forward or rearward portion located in either the inlet or outlet opening. For example, an indicator may be disposed on a surface of the tub six inches away from the rearward portion and the scanner or its field of view are such that the indicator will not be detected until a portion of the tub has traveled through the inlet or outlet opening and the rearward portion is disposed in the corresponding opening (e.g., scanner six inched away from opening). In an alternative embodiment, and for ease of scanner placement the indicators may be located equidistant from both the forward portion and the rearward portion. Non-limiting locations for indicator placement include the tub bottom, side-walls and forward and rearward portions. Moreover, indicator 100 can be used to determine whether a tub without any x-ray shielding is disposed within the structure thus, if the indicator is not detected no signal is generated to allow the x-ray source to be activated (e.g., generate x-rays).

In another exemplary embodiment, the forward portion and the rearward portion of the peripheral wall are each configured to provide a predetermined distance between the receiving area and the x-ray inhibiting material such that an object disposed in the receiving area will be sufficiently spaced away from the x-ray inhibiting material so that the x-ray inhibiting material will not interfere with the scanning of the object. A non-limiting example of this configuration is an angular configuration of the forward or rearward portion or alternatively disposing a step portion 105 of non-x-ray inhibiting material in the receiving area. Examples such step portions or angular configurations are illustrated by the dashed lines in FIG. 7.

Exemplary embodiments of the present invention also contemplate the x-ray inhibiting container to be configured such that it will also pass through a gantry opening of a CT scanner as well as the inlet and outlet openings of the structure as it is placed on the motorized conveyor.

In accordance with another exemplary embodiment of the present invention, a computed tomography system for scanning items is provided, wherein the system will utilize a plurality of the x-ray inhibiting containers along with at least one scanner to detect the presence and location of the container as well as provide a signal to a control system of the CT scanning system.

As shown in the Figures, the system will comprise a computed tomography scanner. The scanner will be configured to produce x-ray projection data of an object as it is passed through the computed tomography scanner. The system will also comprise structure 72, which defines an internal volume configured to receive at least the gantry of the computed tomography scanner therein. The structure further comprising input opening 74 and outlet opening 76, wherein the structure further comprises an x-ray shielding material and motorized conveyor 98 for passing a plurality of tubs 82 through the input opening to the outlet opening.

Referring now to FIGS. 3-7, scanning device 102 is positioned to detect indicator 100 and the presence of one of the plurality of tubs. In accordance with an exemplary embodiment scanner 102 is positioned to detect container 82 when either the forward portion and or the rearward portion of the peripheral wall is positioned to substantially cover the input opening or the outlet opening and the forward portion and the rearward portion of each tub comprises an x-ray shielding material. Thus, the location of one of the tubs proximate to scanner 102 such that indicator 100 is detected will represent a condition wherein the x-ray shielding means of the container is configured to block x-ray leakage from the structure.

In an exemplary embodiment, each of the plurality of tubs are substantially uniform in size and configuration and location of the indicator on each of the tubs is in substantially the same location such that scanner 102 can detect the presence of each tub, wherein the detected presence will coincide with a tub location wherein either the forward or rearward portion of the tub is in an x-ray blocking configuration (e.g., blocking the openings of the structure). In addition, each of the plurality of tubs is configured to provide a predetermined distance between the tub volume of each of the plurality of tubs as they are placed on the motorized conveyor. In other words, the uniform configuration of the tubs will allow for equidistant placement of objects on the motorized conveyor (e.g., objects placed in the tubs).

In accordance with an alternative exemplary embodiment, structure 72 is configured to have a plurality of partitions 104 located at a distance above the motorized conveyor, wherein the distance is such that it allows for un-impeded passage of the plurality of tubs on conveyor 98 underneath partition 104. In an exemplary embodiment, partitions 104 also comprise an x-ray inhibiting material to provide further x-ray shielding in structure 72. In exemplary embodiments, partitions 104 are in a facing spaced relationship such that the distance between each partition substantially aligns with a length of the tubs as they are traveling along on conveyor 98. For example, as a tub travels along conveyor 98 there will be a position wherein the forward portion and the rearward portion of the tub will align with the partitions. Moreover, scanner 102 or a plurality of scanners 102 (as will be discussed herein) are located to detect the position of each tub as it is substantially aligned with the partitions by detecting the presence of the indicator of one of the tubs.

In accordance with an alternative exemplary embodiment, one of the plurality of partitions 104 is located at either the input end or outlet end or both and partition 104 defines a portion or periphery of inlet or outlet openings.

Figure 8:
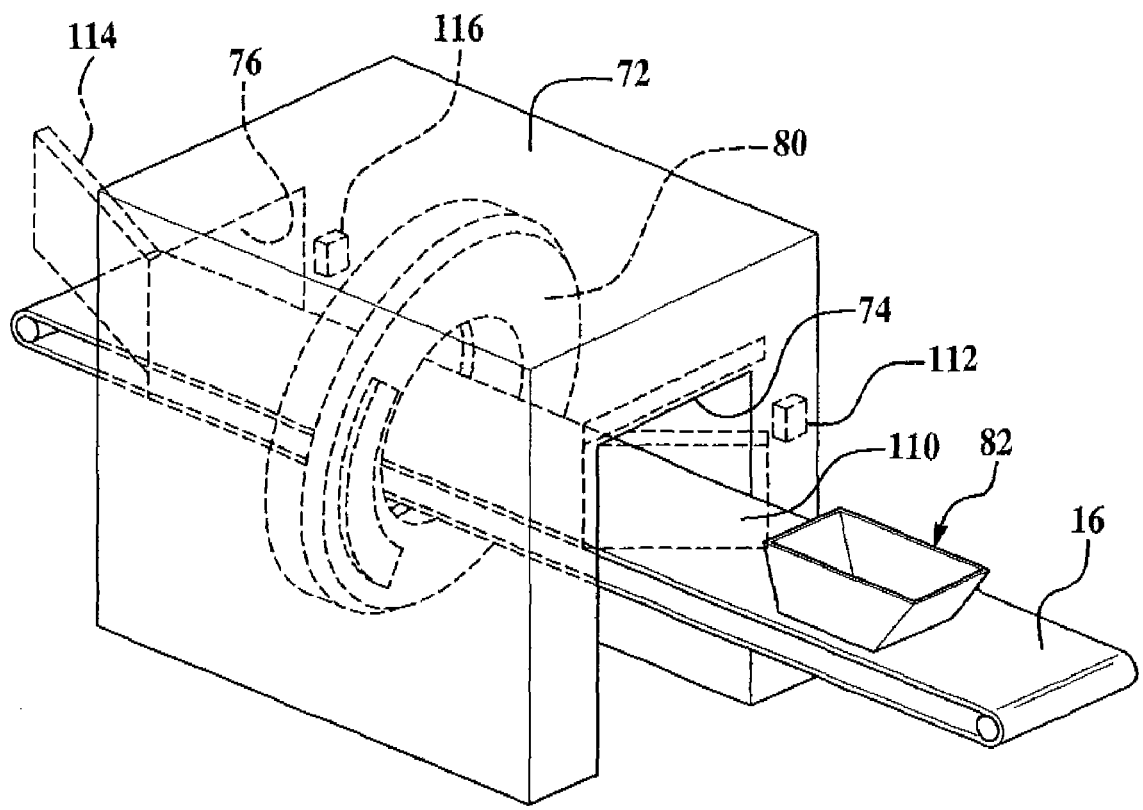
FIG. 8 is a perspective view of a CT scanning system in accordance with an alternative exemplary embodiment of the present invention.

In accordance with yet another alternative exemplary embodiment, and referring now to FIG. 8, structure 72 is configured to have a first door member 110 (illustrated by dashed lines) movably secured proximate to the input opening for movement between an open door position and a closed door position, wherein the first door member also comprises an x-ray inhibiting material and is configured to cover the input opening when the first door member is in the closed door position. In accordance with one exemplary embodiment, first door member is placed in the closed door position when the last of a plurality of tubs is passed through inlet opening and x-ray shielding is required (e.g., no more tubs are placed on the conveyor and as the last tub passes through there is a need to have shielding at the inlet opening). First door member may comprise a door member pivotally mounted to the structure by a plurality of hinges or alternatively a roll up curtain disposed above or beside inlet opening 74. Of course, other door configurations and structures are contemplated for use in exemplary embodiments of the present invention.

In yet another alternative embodiment, and in order to provide a door closed signal to a controller of the CT scanning system, a first switch door switch 112 is disposed proximate to inlet opening 74, wherein the first door switch is configured to provide a door closed signal when the first door member is in the closed door position thus, providing a signal indicative that the x-ray inhibiting material of the first door member is covering the inlet opening. In an exemplary embodiment this signal is provided to a control algorithm of computer 46, wherein the computer will prevent from emitting x-rays unless the door closed signal is received.

Similarly, a second door member 114 (illustrated by dashed lines) in FIG. 8 is movably secured to the outlet opening of the structure for movement between an open door position and a closed door position, wherein the second door member also comprises an x-ray inhibiting material and is configured to cover the outlet opening when the first door member is in the closed door position. In accordance with an exemplary embodiment, second door member is placed in the closed door position when the first of a plurality of tubs is passed through inlet opening and x-ray shielding is required (e.g., no tubs had been previously placed on the conveyor thus, no shielding or a forward or rearward tubs has been positioned at the outlet opening thus, there is a need to have shielding at the outlet opening). As with the first door member, second door member may comprise a door member pivotally mounted to the structure by a plurality of hinges or alternatively a roll up curtain disposed above or besides outlet opening 76.

In yet another alternative embodiment, and in order to provide a door closed signal to a controller of the CT scanning system, a second switch door switch 116 is disposed proximate to outlet opening 76, wherein the second door switch is configured to provide a door closed signal when the second door member is in the closed door position thus, providing a signal indicative that the x-ray inhibiting material of the second door member is covering the outlet opening. In an exemplary embodiment this signal is provided to a control algorithm of computer 46, wherein the computer will prevent the x-ray source from emitting x-rays unless the door closed signal is received. In yet another alternative and when system 70 is experiencing low throughput (e.g., small number of containers passing through) the system may be configured to prevent the x-ray source of generating x-rays unless both the closed door signals (inlet and outlet) are received or a combination of one closed door signal and the detection of one of the indicator of one of plurality of tubs (e.g., forward or rearward portion of the tubs providing x-ray shielding). In addition, any of the aforementioned embodiments may be combined with the plurality of partitions disposed within the structure.

In yet another alternative exemplary embodiment, the CT scanner will be provided with a plurality of scanners each being configured and located to detect the presence of the indicator of one of the plurality of tubs at a discrete location within the structure, wherein a first one of the plurality of scanners provides a first signal when a first one of the plurality of tubs is located proximate to the input opening and the x-ray shielding material of the first tub is disposed within the input opening and a second one of the plurality of scanners is located to provide a second signal when a second one of the plurality of tubs is located proximate to the opening of the gantry (e.g., in a position ready to be scanned) and a third one of the plurality of scanners is positioned to provide a third signal when a third one of the plurality of tubs is disposed proximate to the outlet opening of the structure and the x-ray shield material of the tub is disposed within the outlet opening, wherein the x-ray source is prevented from projecting a fan beam of x-ray unless the first, the second and the third signals are generated.

In other words a plurality of scanners 102 are positioned to generate signals indicating that the x-ray inhibiting material of the tubs is proximate to the structure opening thus giving an "ok to scan" signal to the x-ray controller and the conveyor controller (e.g., allowing conveyor to advance while scanning is occurring). Moreover, the second signal can be used to indicate that a tub with objects disposed therein is ready for scanning. Thereafter, the system may be instructed to stop the conveyor and shut down the x-ray source if another tub is not detected proximate to the inlet opening or alternatively the outlet opening. Moreover, and as discussed above the movable doors and door closure switches may be combined with this embodiment to provide methods for placing x-ray inhibiting material proximate to the openings of the structure. Thus, each of these signals may be presented to a control algorithm of the system wherein go/no-go signals are provided to at least the conveyor controller and the x-ray controller as well as the gantry controller. Again, and as in the previous embodiments, the partitions 104 may be combined with the aforementioned alternative embodiments. Schematic illustrations of these sensors are provided in FIG. 2, it being understood that any combination of sensors/scanners 102, 112 and 116 may be used in exemplary embodiments of the present invention.

Figure 9:
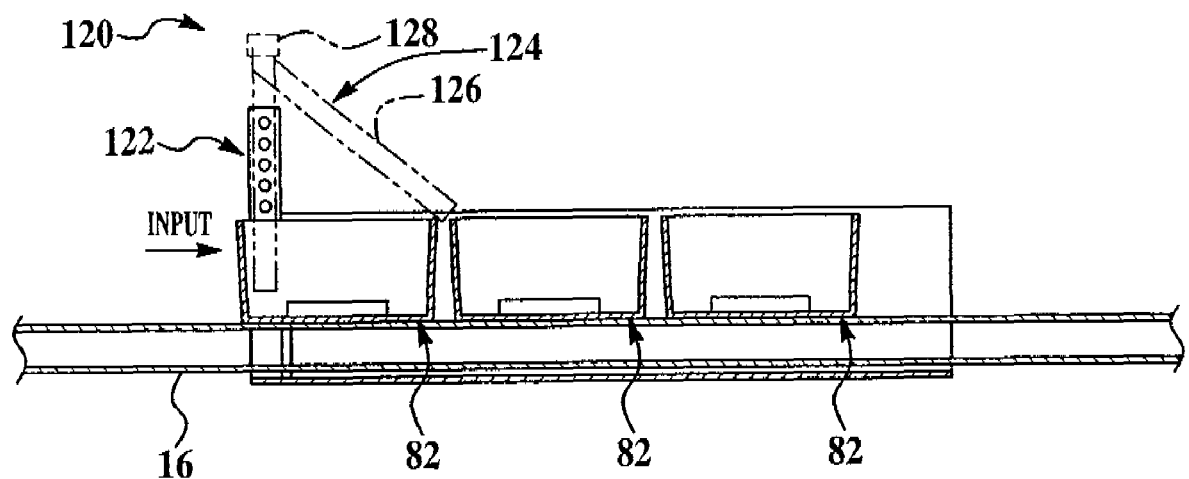
FIG. 9 is a partial side view of a CT scanning system in accordance with an alternative exemplary embodiment of the present invention.

In yet another alternative exemplary embodiment, and referring now to FIG. 9 and in lieu of scanner(s) 102 and indicator 100, a deflectable switching member 120 is positioned for movement between an empty conveyor position 122 and an occupied conveyor position 124. The deflectable switching member providing an empty conveyor signal when the deflectable switching member is in the empty conveyor position, wherein the x-ray source is prevented from projecting the fan beam of x-ray when the empty conveyor signal is generated. The deflectable switching member being configured and positioned to be moved from the empty conveyor position to the occupied conveyor position by one of the plurality of tubs as it passes through the system on the motorized conveyor. In one exemplary embodiment, the deflectable switching member comprises a deflectable arm 126 coupled to a micro-switch 128 configured to provide a signal as the deflectable arm is moved from the empty conveyor position to the occupied conveyor position. As illustrated, deflectable switching member 128 and the plurality of tubs are configured to provide the occupied conveyor signal when the x-ray shielding material of at least one of the plurality of tubs is located at either the input opening or the outlet opening of the structure. Moreover, the distal portion of deflectable arm 126 is configured such that it will only travel to an unoccupied conveyor position when a container is not proximate to the opening (e.g., distal end is configured such that it cannot drop within the receiving area of the container i.e., width of deflectable arm greater than a width of the container).

In yet another alternative exemplary embodiment, deflectable switching member 120 may be used in conjunction with any combination of sensors/scanners 102, 112 and 116 and tubs 82 with indicators 100, wherein deflectable switching member 120 provides a mechanical backup to scanner 102.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the present application.

What is claimed is:

1. A computed tomography (CT) scanning system for scanning objects, said CT scanning system comprising:
   a structure at least partially defining a passage having an input opening and an outlet opening, said structure comprising a radiation shielding material;
   a gantry positioned within said structure, said gantry defining a gantry opening;
   a radiation source coupled to said gantry and configured to project a radiation beam towards a detector array coupled to said gantry on an opposite side of said gantry opening from said radiation source; and
   a conveyor configured to pass a plurality of tubs through said passage and said gantry opening, each tub of said plurality of tubs comprising a peripheral wall having a forward portion and a rearward portion configured to substantially block one of said input opening and said outlet opening as said plurality of tubs are passed through said structure, said forward portion and said rearward portion each comprising a radiation shielding material.

2. A CT scanning system in accordance with claim 1, wherein said structure is configured to allow for scanning of an object passing through said structure.

3. A CT scanning system in accordance with claim 1, wherein said x-ray source and said detector array are rotatably mounted about said gantry opening.

4. A CT scanning system in accordance with claim 1, wherein each tub further comprises a pair of side walls extending between said forward portion and said rearward portion.

5. A CT scanning system in accordance with claim 1, further comprising an indicator coupled to each tub at a select location.

6. A CT scanning system in accordance with claim 5, further comprising at least one scanner configured to detect said indicator at a predetermined location within said structure.

7. A CT scanning system in accordance with claim 5, wherein a first scanner of said at least one scanner generates a first signal when the radiation shielding material of a first tub of said plurality of tubs is positioned within said input opening, a second scanner of said at least one scanner generates a second signal when a second tub of said plurality of tubs is located proximate to said gantry opening, and a third scanner of said at least one scanner generates a third signal when the radiation shield material of a third tub of said plurality of tubs is positioned within said outlet opening.

8. A CT scanning system in accordance with claim 7, wherein said radiation source is prevented from projecting the radiation beam until said first signal, said second signal, and said third signal are generated.

9. A method for shielding radiation within a computed tomography (CT) scanning system, said method comprising advancing a plurality of tubs through a passage defined by the CT scanning system having an input opening and an outlet opening, wherein each tub of the plurality of tubs includes a peripheral wall having a forward portion and a rearward portion configured to substantially block one of the input opening and the outlet opening, wherein each of the forward portion and the rearward portion includes a radiation shielding material.

10. A method in accordance with claim 9, further comprising positioning an indicator on an outer surface of each tub.

11. A method in accordance with claim 10, further comprising determining a location of each tub advancing through the CT scanning system by scanning for the indicator.

12. A method in accordance with claim 9, further comprising generating an output signal when one of the input opening and the outlet opening is covered by one of the forward portion and the rearward portion of one tub of the plurality of tubs.

13. A method in accordance with claim 12 further comprising preventing an x-ray source of the CT scanning system from generating a radiation beam unless the output signal is generated.

* * * * *